United States Patent
Guimaraes et al.

(10) Patent No.: US 7,311,700 B2
(45) Date of Patent: Dec. 25, 2007

(54) LASIK LAMINAR FLOW SYSTEM

(75) Inventors: Ricardo Guimaraes, Belo Horizonte (BR); Rod Ross, Mission Viejo, CA (US)

(73) Assignee: Med-Logics, Inc., Laguna Hills, CA (US)

(*) Notice: Subject to any disclaimer, the term of this patent is extended or adjusted under 35 U.S.C. 154(b) by 567 days.

(21) Appl. No.: 09/726,953

(22) Filed: Nov. 29, 2000

(65) Prior Publication Data

US 2002/0065510 A1    May 30, 2002

(51) Int. Cl.
*A61N 5/06* (2006.01)
*A61B 17/36* (2006.01)

(52) U.S. Cl. ............ 606/4; 606/5; 606/10; 623/107

(58) Field of Classification Search .......... 606/2–6, 606/10–13, 17, 19, 107, 166; 623/4.1, 4.5, 623/5.11, 107; 359/368, 372, 379, 380–382; 604/23, 35

See application file for complete search history.

(56) References Cited

U.S. PATENT DOCUMENTS

| | | | |
|---|---|---|---|
| 1,841,968 A | 1/1932 | Lowry |
| 1,847,658 A | 3/1932 | Lasker |
| 2,070,281 A | 2/1937 | Leggiadro |
| 2,480,737 A | 8/1949 | Jayle |
| RE23,496 E | 5/1952 | Seeler |
| 2,708,437 A | 5/1955 | Hutchins |
| 2,824,455 A | 2/1958 | Ristow et al. |
| 3,033,196 A | 5/1962 | Hay |
| 3,252,623 A | 5/1966 | Corbin et al. |
| 3,266,494 A | 8/1966 | Brownrigg et al. |
| 3,308,828 A | 3/1967 | Pippin |
| 3,399,677 A | 9/1968 | Gould et al. |
| 3,561,429 A | 2/1971 | Jewett |
| 3,583,403 A | 6/1971 | Pohl |
| 3,589,363 A | 6/1971 | Banko |
| 3,624,821 A | 11/1971 | Henderson |
| 3,693,613 A | 9/1972 | Kelman |
| 3,723,030 A | 3/1973 | Gelfand |
| 3,752,161 A | 8/1973 | Bent |

(Continued)

FOREIGN PATENT DOCUMENTS

DE    25 47 185    4/1997

(Continued)

OTHER PUBLICATIONS

Steinway Instrument Company Inc., The Steinway/Barraquer in-Situ Microkeratome Set.

(Continued)

*Primary Examiner*—Justine R. Yu
*Assistant Examiner*—Shumaya Ali
(74) *Attorney, Agent, or Firm*—The Eclipse Group LLP

(57) ABSTRACT

A system that can be used to perform an ophthalmic procedure. The system may include a patient support that supports a patient and a light source which can direct a beam of light onto the patient's cornea. The system may also include an airflow module that directs a flow of air above the cornea. The flow of air reduces the amount of contaminants that may become attached to the cornea during the procedure.

5 Claims, 1 Drawing Sheet

U.S. PATENT DOCUMENTS

| | | |
|---|---|---|
| 3,763,862 A | 10/1973 | Spieth |
| 3,806,720 A * | 4/1974 | Hortig ........................ 362/253 |
| 3,812,855 A | 5/1974 | Banko |
| 3,815,604 A | 6/1974 | O'Malley et al. |
| 3,841,799 A | 10/1974 | Spinosa et al. |
| 3,842,839 A | 10/1974 | Malis et al. |
| 3,882,872 A | 5/1975 | Douvas et al. |
| 3,884,238 A | 5/1975 | O'Malley et al. |
| 3,899,829 A | 8/1975 | Storm et al. |
| 3,903,881 A | 9/1975 | Weigl |
| 3,913,584 A | 10/1975 | Walchle et al. |
| 3,920,014 A | 11/1975 | Banko |
| 3,923,482 A * | 12/1975 | Knab et al. ................... 55/412 |
| 3,930,505 A | 1/1976 | Wallach |
| 3,977,425 A | 8/1976 | Hayashida |
| 3,982,539 A | 9/1976 | Muriot |
| 3,983,474 A | 9/1976 | Kuipers |
| 3,986,512 A | 10/1976 | Walliser |
| 4,004,590 A | 1/1977 | Muriot |
| 4,011,869 A | 3/1977 | Seiler, Jr. |
| 4,034,712 A | 7/1977 | Duncan |
| 4,043,342 A | 8/1977 | Morrison, Jr. |
| 4,108,182 A | 8/1978 | Hartman et al. |
| 4,135,515 A | 1/1979 | Muriot |
| 4,137,920 A | 2/1979 | Bonnet |
| 4,168,707 A | 9/1979 | Douvas et al. |
| 4,173,980 A | 11/1979 | Curtin |
| 4,178,707 A | 12/1979 | Littlefield |
| 4,204,328 A | 5/1980 | Kutner |
| 4,205,682 A | 6/1980 | Crock et al. |
| 4,210,146 A | 7/1980 | Banko |
| 4,217,993 A | 8/1980 | Jess et al. |
| 4,223,676 A | 9/1980 | Wuchinich et al. |
| 4,245,815 A | 1/1981 | Willis |
| 4,246,902 A | 1/1981 | Martinez |
| 4,274,411 A | 6/1981 | Dotson, Jr. |
| 4,301,802 A | 11/1981 | Poler |
| 4,304,262 A | 12/1981 | Icking |
| 4,308,385 A | 12/1981 | Goorden |
| 4,308,835 A | 1/1982 | Abbey |
| 4,314,560 A | 2/1982 | Helfgott et al. |
| 4,320,761 A | 3/1982 | Haddad |
| 4,354,838 A | 10/1982 | Hoyer et al. |
| 4,395,258 A | 7/1983 | Wang et al. |
| 4,396,386 A | 8/1983 | Kurtz et al. |
| 4,428,748 A | 1/1984 | Peyman et al. |
| 4,429,696 A | 2/1984 | Hanna |
| 4,445,517 A | 5/1984 | Feild |
| 4,474,411 A | 10/1984 | Peters et al. |
| 4,475,904 A | 10/1984 | Wang |
| 4,476,862 A | 10/1984 | Pao |
| 4,479,717 A | 10/1984 | Cornillault |
| 4,481,948 A | 11/1984 | Sole |
| 4,493,695 A | 1/1985 | Cook |
| 4,493,698 A | 1/1985 | Wang et al. |
| 4,522,371 A | 6/1985 | Fox et al. |
| 4,523,911 A | 6/1985 | Braetsch et al. |
| 4,524,948 A | 6/1985 | Hall |
| 4,530,357 A | 7/1985 | Pawloski et al. |
| 4,531,934 A | 7/1985 | Kossovsky et al. |
| 4,540,406 A | 9/1985 | Miles |
| 4,555,645 A | 11/1985 | Atkinson |
| 4,589,414 A | 5/1986 | Yoshida et al. |
| 4,598,729 A | 7/1986 | Naito et al. |
| 4,647,209 A | 3/1987 | Neukomm et al. |
| 4,660,556 A | 4/1987 | Swinger et al. |
| 4,660,970 A | 4/1987 | Ferrano |
| 4,662,370 A | 5/1987 | Hoffmann et al. |
| 4,665,914 A | 5/1987 | Tanne |
| 4,674,499 A | 6/1987 | Pao |
| 4,674,503 A | 6/1987 | Peyman et al. |
| 4,678,459 A | 7/1987 | Onik et al. |
| 4,688,570 A | 8/1987 | Kramer et al. |
| 4,690,099 A | 9/1987 | Gregan et al. |
| 4,701,049 A | 10/1987 | Beckmann et al. |
| 4,705,395 A | 11/1987 | Hageniers |
| 4,706,687 A | 11/1987 | Rogers |
| 4,723,545 A | 2/1988 | Nixon et al. |
| 4,743,770 A | 5/1988 | Lee |
| 4,757,814 A | 7/1988 | Wang et al. |
| 4,767,403 A | 8/1988 | Hodge |
| 4,768,506 A | 9/1988 | Parker et al. |
| 4,770,654 A | 9/1988 | Rogers et al. |
| 4,782,239 A | 11/1988 | Hirose et al. |
| 4,782,849 A | 11/1988 | Hodge |
| 4,791,934 A | 12/1988 | Brunnett |
| 4,805,615 A | 2/1989 | Carol |
| 4,805,616 A | 2/1989 | Pao |
| 4,807,623 A | 2/1989 | Lieberman |
| 4,819,635 A | 4/1989 | Shapiro |
| 4,825,091 A | 4/1989 | Breyer et al. |
| 4,828,306 A | 5/1989 | Blatt |
| 4,830,047 A | 5/1989 | Hodge |
| 4,837,857 A | 6/1989 | Scheller et al. |
| 4,838,281 A | 6/1989 | Rogers et al. |
| 4,840,175 A | 6/1989 | Peyman |
| 4,865,033 A | 9/1989 | Krumeich et al. |
| 4,881,543 A * | 11/1989 | Trembly et al. ............... 606/27 |
| 4,884,570 A | 12/1989 | Krumeich et al. |
| 4,886,085 A | 12/1989 | Miller |
| 4,903,695 A | 2/1990 | Warner et al. |
| RE33,250 E | 7/1990 | Cook |
| 4,943,289 A | 7/1990 | Goode et al. |
| 4,965,417 A | 10/1990 | Massie |
| 4,988,347 A | 1/1991 | Goode et al. |
| 4,997,437 A | 3/1991 | Grieshaber |
| 5,011,482 A | 4/1991 | Goode et al. |
| 5,013,310 A | 5/1991 | Goode et al. |
| 5,019,076 A | 5/1991 | Yamanashi et al. |
| 5,059,204 A | 10/1991 | Lawson et al. |
| 5,106,364 A | 4/1992 | Hayafuji et al. |
| 5,133,713 A | 7/1992 | Huang et al. |
| 5,133,726 A | 7/1992 | Ruiz et al. |
| 5,176,628 A | 1/1993 | Charles et al. |
| 5,201,749 A | 4/1993 | Sachse et al. |
| 5,207,683 A | 5/1993 | Goode et al. |
| 5,215,104 A | 6/1993 | Steinert |
| 5,217,459 A | 6/1993 | Kamerling |
| 5,226,910 A | 7/1993 | Kajiyama et al. |
| 5,242,404 A | 9/1993 | Conley et al. |
| 5,271,379 A | 12/1993 | Phan et al. |
| 5,273,406 A | 12/1993 | Feygin |
| 5,273,524 A | 12/1993 | Fox et al. |
| 5,285,795 A | 2/1994 | Ryan et al. |
| 5,322,505 A | 6/1994 | Krause et al. |
| 5,330,470 A | 7/1994 | Hagen |
| 5,354,268 A | 10/1994 | Peterson et al. |
| 5,364,395 A | 11/1994 | West, Jr. |
| 5,374,188 A | 12/1994 | Frank et al. |
| 5,380,280 A | 1/1995 | Peterson |
| 5,383,454 A | 1/1995 | Bucholz |
| 5,395,368 A | 3/1995 | Ellman et al. |
| 5,403,276 A | 4/1995 | Schechter et al. |
| 5,403,311 A | 4/1995 | Abele et al. |
| 5,437,678 A | 8/1995 | Sorensen |
| 5,465,633 A | 11/1995 | Bernloehr |
| 5,474,532 A | 12/1995 | Steppe |
| 5,476,448 A | 12/1995 | Urich |
| 5,476,473 A | 12/1995 | Heckele |
| 5,496,339 A | 3/1996 | Koepnick |
| 5,507,751 A | 4/1996 | Goode et al. |
| 5,520,684 A | 5/1996 | Imran |
| 5,527,332 A | 6/1996 | Clement |
| 5,527,356 A | 6/1996 | Peyman et al. |

| | | | |
|---|---|---|---|
| 5,531,744 | A | 7/1996 | Nardella et al. |
| 5,556,397 | A | 9/1996 | Long et al. |
| 5,566,681 | A | 10/1996 | Manwaring et al. |
| RE35,421 | E | 1/1997 | Ruiz et al. |
| D377,524 | S | 1/1997 | Lipp |
| 5,611,799 | A | 3/1997 | Smith |
| 5,624,394 | A | 4/1997 | Barnitz et al. |
| 5,643,304 | A | 7/1997 | Schechter et al. |
| 5,693,013 | A | 12/1997 | Geuder |
| 5,700,240 | A | 12/1997 | Barwick, Jr. et al. |
| 5,704,927 | A | 1/1998 | Gillette et al. |
| 5,738,677 | A | 4/1998 | Colvard et al. |
| 5,755,700 | A * | 5/1998 | Kritzinger et al. ............ 604/35 |
| 5,779,723 | A | 7/1998 | Schwind |
| 5,782,849 | A | 7/1998 | Miller |
| 5,787,760 | A | 8/1998 | Thorlakson |
| 5,795,328 | A | 8/1998 | Barnitz et al. |
| 5,810,857 | A | 9/1998 | Mackool |
| 5,814,010 | A | 9/1998 | Ziegler |
| 5,817,075 | A | 10/1998 | Giungo |
| 5,868,728 | A | 2/1999 | Giungo et al. |
| 5,916,330 | A | 6/1999 | Jacobson |
| 5,934,285 | A * | 8/1999 | Kritzinger et al. .......... 606/166 |
| 5,941,250 | A | 8/1999 | Aramant et al. |
| 5,944,731 | A | 8/1999 | Hanna |
| 5,957,921 | A | 9/1999 | Mirhashemi et al. |
| 5,984,913 | A * | 11/1999 | Kritzinger et al. .......... 606/107 |
| 5,989,272 | A | 11/1999 | Barron et al. |
| 6,004,313 | A * | 12/1999 | Shimmick et al. ............. 606/5 |
| 6,013,049 | A | 1/2000 | Rockley et al. |
| 6,019,754 | A * | 2/2000 | Kawesch ....................... 606/4 |
| 6,045,563 | A | 4/2000 | Duprat |
| 6,051,009 | A | 4/2000 | Hellenkamp et al. |
| 6,059,805 | A | 5/2000 | Sugimura et al. |
| 6,083,236 | A | 7/2000 | Feingold |
| 6,086,544 | A | 7/2000 | Hibner et al. |
| 6,165,189 | A | 12/2000 | Ziemer |
| 6,251,101 | B1 * | 6/2001 | Glocker .......................... 606/5 |
| 6,258,082 | B1 * | 7/2001 | Lin ................................ 606/5 |
| 6,312,403 | B1 * | 11/2001 | Ruiz ........................... 604/23 |
| 6,406,473 | B1 * | 6/2002 | Shimmick et al. ............. 606/5 |

FOREIGN PATENT DOCUMENTS

| | | |
|---|---|---|
| EP | 1033 120 A2 | 6/2000 |
| FR | 2 549 727 | 7/1963 |

OTHER PUBLICATIONS

Brochure, Site TXR Systems, Site Mycrosurgical Systems, Inc., Horsham, Pennsylvania.

Marshall M. Parks, "Intracapsular Aspiration" article, pp. 59-74.

Van Oldenborgh, "Correction of late operative complications by means of a suction cutter", Opthal. Soc. U.K. (1980), 100, 219, pp. 219-221.

Helfgott, M.D. "A System for Variable Aspiration of Material Dissected from the Posterior Chamber", Ophthalmic Surgery, vol. 15, Jun. 1984, pp. 529-350.

Coopervision Brochure on Cavitron/Kelman Model 6500 E.I.S. and Model 7500, 6 pages.

Surgical Design Brochure on "The Ocusystem", 1 page.

Coopervision Brochure on "Cavitorn/Kelman Phaco-Emulsifier Aspirator Model 8001", 2 pages.

Coopervision Brochure on Cavitron/Kelman Phaco-Emulsifier Aspirator Model 9001, 6 pages.

Greishaber of Switzerland Brochure on "MPC, The Membrane Peeler Cutter", 5 pages.

Micro-Vit Vitrectomy System Product Brochure and Instruction Manual.

Storz Irrigation Aspiration System Product Brochure and Instruction Manual.

United Surgical Corporation Brochure on "Phacotron Plus", one page.

Surgical Design Company Brochure on Keates Ultrasonic I/E Mini Probe by A. Banko, 2 pages.

Surgical Design Corporation Brochure on U.S., Phaco System, 1 page.

Coopervision Brochure on System VI, 1 page.

Murayama et al. "A Portable Air Driving Unit for Blood Pumps", Japanese Journal of Artificial Organs, vol. 14, No. 3, pp. 1206-1209 (English Translation).

Scuderi, et al., French article entitled "La Chirurgie de la Cartaracte Congenitale", pp. 174-185. (English translation).

Hayashi et al., Japanese Experience with Ventricular Assist Devices IBEE Engineering in Medicine and Biology Magazine Mar. 1986, pp. 30-36.

Grieshaber and Co. of Switzerland, "Sutherland Rotatable Intraocular Microscissors", 2 pages.

Jcers and Tissue Removal Systems, Diskecter™ System, Rapid Tissue Removal System advertisement.

Charles and Wang, "A Linear Suction Control for the Vitreous Cutter (Ocutome)", Arch. Ophthalmol. vol. 99, Sep. 1981, p. 1631.

Crosby, "On Control of Artificial Hearts", pp. 89-114.

Mrava, Cardiac Engineering, vol. 3, pp. 31-68.

* cited by examiner

LASIK LAMINAR FLOW SYSTEM

BACKGROUND OF THE INVENTION

1. Field of the Invention

The present invention relates to an air flow system that can reduce the amount of contaminates at the site of an ophthalmic procedure.

2. Background Information

There have been developed various techniques for correcting the vision of a patient. For example, there is a medical procedure that varies the curvature of a cornea using a laser. This procedure is commonly referred to as Laser in situ Keratomileusis (LASIK).

In a LASIK procedure, a surgeon cuts the cornea to create a flap. The flap is peeled back to expose the stroma layer of the cornea. A laser beam is then directed into the stroma to ablate the cornea and vary the refractive characteristics of the eye. After the ablation step, the flap is placed back onto the cornea to complete the procedure. LASIK procedures are typically performed in a room that may have dust particles and other contaminants. The contaminants may become attached to the stroma and lead to a post-operative infection of the eye. The stroma tissue has a tendency to attract and retain contaminants. Additionally, the ablated stroma is sometimes aspirated so that the patient does not smell burning tissue. Unfortunately, aspirating the burned tissue pulls air and accompanying contaminants into the eye.

To reduce the amount of contaminants introduced to the cornea during a procedure the surgeon will frequently apply an irrigation fluid to the eye. The irrigation fluid may over-hydrate the cornea and possibly interfere with the ablation of the stroma by the laser beam. It would be desirable to provide a system that can reduce the amount of contaminants introduced to a cornea in an ophthalmic procedure.

BRIEF SUMMARY OF THE INVENTION

One embodiment of the present invention is a system that can be used to perform an ophthalmic procedure. The system may include a patient support that supports a patient and a light source, which can direct a beam of light onto the patient's cornea. The system may also include an airflow module that directs a flow of air above the cornea.

DETAILED DESCRIPTION OF THE PREFERRED EMBODIMENT

One embodiment of the present invention provides an airflow module that can direct a flow of air across the cornea of a patient during a LASIK procedure. The flow of air reduces the amount of contaminants that may become attached to the cornea during the procedure.

Figure 1:
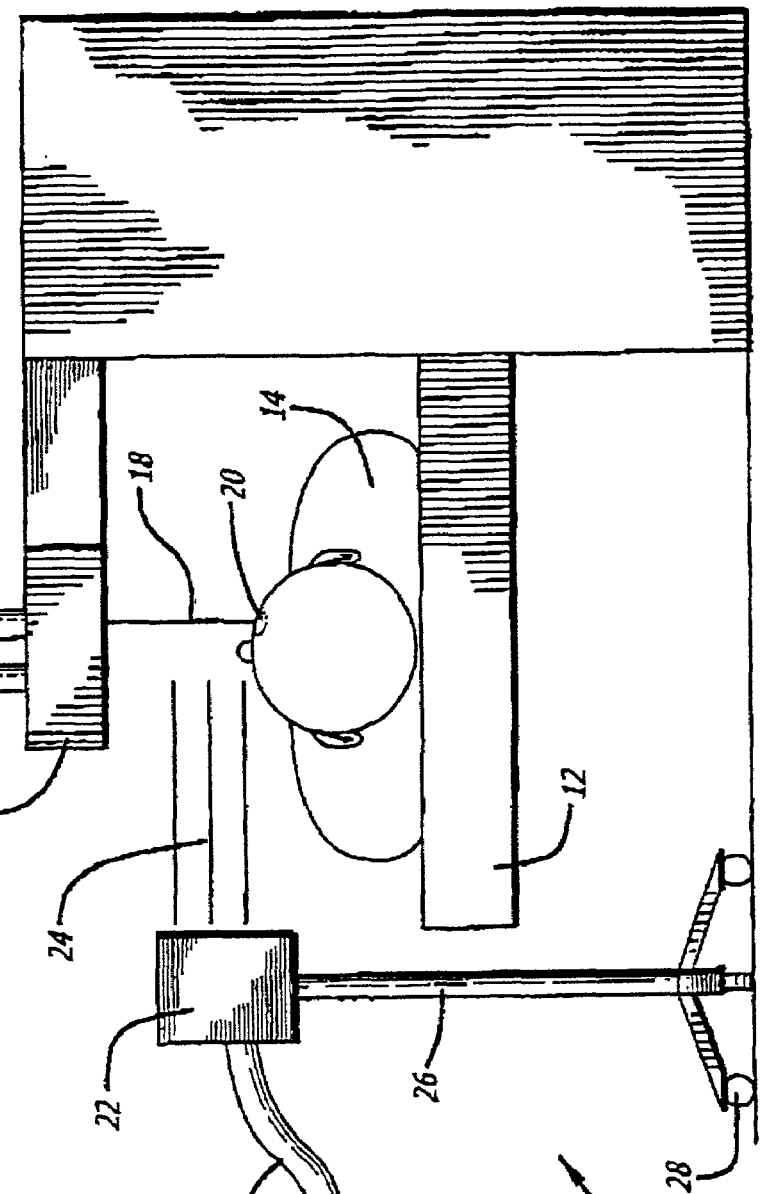
FIG. 1 is an illustration showing an embodiment of a system of the present invention.

Referring to the drawings more particularly by reference numbers, FIG. 1 shows an embodiment of a system 10 of the present invention. The system 10 may include a patient support 12 that supports a patient 14. The patient support 12 may be a table. Alternatively, the support 12 may be a chair or any other support structure.

The system 10 may further include a light source 16 that directs a beam of light 18 onto a cornea 20 of the patient 14. The light source 16 may be an Eximer laser that emits light at a wavelength, which ablates corneal tissue.

The system 10 may include an airflow module 22 that directs a flow of air 24 across the patient's cornea 20. The airflow module 22 may be supported by a stand 26. The stand 26 may have wheels 28 that allow an operator to move the module 22 relative to the support 12 and the patient 14.

The airflow module 22 way be coupled to a control console 30 by an air hose 32. The control console 30 may be coupled to a source of pressurized air (not shown) that provides a flow of air. By way of example, the source of pressurized air may be an air line in the building structure of the surgical site. Alternatively, the console 30 may contain a compressor to create a pressurized airflow.

The console 30 may include a control knob 34 that can be manipulated by an operator to control the flowrate of the air that flows across the cornea 20. The knob 34 may be coupled to a valve (not shown) that can vary the flowrate. The console 30 may also have a readout 36 that displays the flowrate and/or pressure of the airflow.

Figure 2:
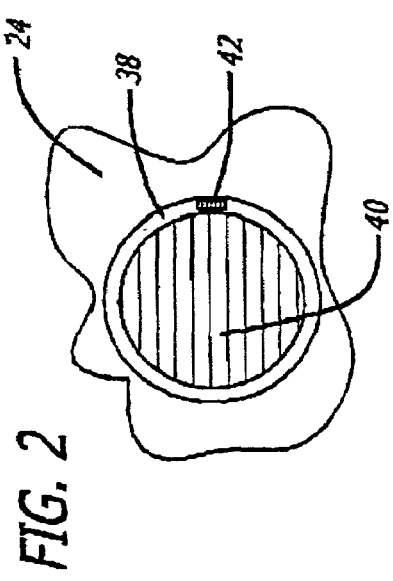
FIG. 2 is an illustration showing an airflow module of the system.

FIG. 2 shows an embodiment of the air flow module 22. The module 22 may have an outlet 38 designed to generate a laminar flow of air across the cornea. Laminar airflow will create an airstream that will flow directly above the cornea 20. A laminar airflow is preferred over turbulent flow which may allow contaminants to enter the region of the cornea 20. The outlet 38 may have one or more vent blades 40 that can be adjusted to vary the direction of the airflow. The orientation of the blades 40 and the direction of airflow may be adjusted by manipulating wheel 42. cornea 20. A laminar airflow is preferred over turbulent flow which may allow contaminants to enter the region of the cornea. The outlet 38 may have one or more vent blades 40 that can be adjusted to vary the direction of the airflow. The orientation of the blades 40 and the direction of airflow may be adjusted by manipulating wheel 42.

In operation, the module 22 is moved adjacent to the patient 14, and the console 30 and/or blades 40 are adjusted to create a desired flow of air directly above the cornea 20. It is desirable to create an airflow tat does not directly impinge the cornea 20 to prevent corneal dehydration.

After the desired airflow is created, a surgeon creates a flap to expose the stroma of the cornea 20. The laser is then excited to create the light beam 18 and ablate the cornea 20. After the cornea 20 has been ablated, the flap is moved back to cover the exposed stioma. The airflow is then terminated and the module 22 is moved away from the support 12 so that the patient 14 can exit the surgical site.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for performing an ophthalmic procedure on a cornea of a patient, comprising:

operating an air flow module including an outlet and a plurality of vent blades adjustably mounted to the outlet, wherein operating includes adjusting the vent blades to direct a laminar flow of air from the outlet, around the vent blades, and above the cornea from one side of the cornea to another side of the cornea, at a distance so that the cornea is not de-hydrated by the flow of air;

creating a flap in the cornea;

moving the flap to expose a portion of the cornea;

ablating a portion of the exposed cornea with a laser beam; and moving the flap back onto the cornea.

2. The method of claim 1, further comprising adjusting a flowrate of the flow of air.

3. The method of claim 1, further comprising adjusting a direction of the flow of air.

4. The method of claim 1, wherein adjusting the vent blades includes rotating a wheel relative to the outlet, the vent blades being mounted to the wheel.

5. The method of claim 1, wherein the air flowing from the outlet has a significant horizontal component.

* * * * *